United States Patent
Kitajima et al.

[11] Patent Number: 6,072,623
[45] Date of Patent: Jun. 6, 2000

[54] SLIT LAMP MICROSCOPE

[75] Inventors: Nobuaki Kitajima; Kazuyuki Okamura, both of Tokyo, Japan

[73] Assignee: Kabushiki Kaisha, Topcon, Tokyo, Japan

[21] Appl. No.: 09/208,973

[22] Filed: Dec. 11, 1998

[30] Foreign Application Priority Data

Dec. 12, 1997 [JP] Japan ................................. 9-343338

[51] Int. Cl.⁷ .................................................. G02B 21/00
[52] U.S. Cl. .......................... 359/368; 359/385; 351/221
[58] Field of Search ................................... 359/368, 370, 359/372, 381, 385, 387, 389, 232; 351/206, 207, 214, 221

[56] References Cited

U.S. PATENT DOCUMENTS

| | | | |
|---|---|---|---|
| 2,427,689 | 9/1947 | Osterberg et al. | 359/370 |
| 3,948,585 | 4/1976 | Heine et al. | 351/13 |
| 4,370,033 | 1/1983 | Kani et al. | 351/206 |
| 4,422,736 | 12/1983 | Nunokawa | 351/207 |
| 4,715,704 | 12/1987 | Biber et al. | 351/207 |
| 5,270,747 | 12/1993 | Kitajima et al. | 351/205 |
| 5,349,398 | 9/1994 | Koester | 351/212 |
| 5,436,679 | 7/1995 | Ohtsuka et al. | 351/206 |

*Primary Examiner*—Cassandra Spyrou
*Assistant Examiner*—Mark A. Robinson
*Attorney, Agent, or Firm*—Armstrong, Westerman, Hattori, McLeland & Naughton

[57] ABSTRACT

A slit lamp microscope of the present invention is provided in which it is possible to observe and record a clear image of the lesion portion of the eye to be examined with a high contrast, and at the same time, it is possible to observe and record the peripheral portion of the eye to be examined. The slit lamp microscope has a first illumination system for projecting local illumination light to the eye to be examined for observing a cross section of the observation portion. A second illumination system is provided with a diaphragm for limiting the illumination filed of the illumination light projected to the eye, for illuminating a peripheral portion of the illumination field of the eye projected by the first illumination system. This makes it possible to observe that the cross section and peripheral portion of the observation portion.

3 Claims, 6 Drawing Sheets

SLIT LAMP MICROSCOPE

BACKGROUND OF THE INVENTION

1. Field of the Invention

The present invention relates to a slit lamp microscope, and more particularly to a slit lamp microscope in which an illumination optical system is improved so that not only a slit image of a specific part, to be observed, of an eye to be medically examined but also a peripheral portion of the part to be observed may be clearly observed.

2. Description of the Related Art

A slit lamp microscope is used as a kind of microscopes for the use in an ophthalmic field. This is used by an ophthalmologist for his or her routine medical examination. A variety of lesion portions of the eye to be examined may be observed through the microscope by devising the illumination method.

As shown in FIG. 9 in concept, in this slit lamp microscope, a ray of light from a light source 201 is formed into a slit-like beam (slit beam) and projected to a cornea Ed of the eye E to be examined so that the cornea Ed is brought into an optically cut condition, and a reflected ray from the corneal portion which has been optically cut is introduced into an observation optical system (not shown) and an image processing system (not shown) through an objective lens 202. As shown in FIG. 10, the corneal sectional image Ed' is displayed on a screen of an image monitor 203. The slit lamp microscope may be used to observe a slight lesion portion of the eye E to be examined by utilizing the Tyndall effect (see "SLIT LAMP" by Motoichi Itoi and Sadao Kanakami, p25, FIG. 34, published by Medical Aoi Publication Co.).

However, in case of such a conventional slit lamp microscope, for example, the corneal cross sectional image Ed' may be clearly observed but the tissue (sclera, iris or the like) except for the corneal cross section cannot be observed at all. This is because the cornea is projected by the slit-like illumination light so that the illumination field is very narrow and the peripheral region except for the corneal cross section becomes so dark (indicated by the cross-hatchings in FIG. 10) so that the region can not be be imaged.

However, if the tissue condition of the peripheral portion around the specific portion of the eye E to be examined is imaged and a position and a size of the lesion portion over the entire eye to be examined may be known, it is possible to perform a suitable examination. Accordingly, it is highly demanded to make it possible to observe the tissue condition of the peripheral portion around some specific portion.

If this is met, it is also advantageous to facilitate the explanation of the lesion portion to a third party except for the patient (i.e., family members of the patient, the persons having to do with some symposium or special magazine or the like).

Under such circumstances, conventionally, a means for projecting another ray of illumination light for illuminating the overall eye to be examined is provided separately from the ray of the slit-like illumination light. The eye to be examined is simultaneously projected by the slit-like illumination light and the other illumination light to thereby image the entire image of the eye to be examined.

However, in the case where the illumination light for the overall eye to be examined is added, the contrast of the image of the lesion portion by the projection of the slit-like illumination light is degraded, resulting in degradation of the image quality. Accordingly, it is troublesome to make a clear examination to the lesion portion of the eye to be examined.

SUMMARY OF THE INVENTION

Accordingly, an object of the present invention is to provide a slit lamp microscope in which a clear image having a high contrast may be observed and recorded for a local lesion portion of an eye to be examined and also the entire eye including the peripheral portion of the lesion portion may be clearly observed and recorded simultaneously therewith.

According to a first aspect of the invention, there is provided a slit lamp microscope characterized by comprising: a first illumination system for projecting local illumination light to an eye to be examined for observing a cross section of an observation portion of the eye to be examined; and a second illumination system provided with an illumination field limiting mechanism portion of the illumination light projected to the eye to be examined for illuminating a peripheral portion of the illumination field of the eye to be examined by the first illumination system for enabling to observe the peripheral portion of the observation portion.

According to this aspect, since the cross section of the observation portion of the eye to be examined is observed by projecting the local illumination light to the eye to be examined by the first illumination system, and at the same time, the peripheral portion of the observation portion may be observed by utilizing the illumination field limiting mechanism portion of the second illumination system and illuminating, by the second illumination system, the peripheral portion of the illumination field of the eye to be examined by the first illumination system, it is possible to observe and record a clear image of the lesion portion of the eye to be examined with a high contrast on the basis of the local illumination light, and it is possible to observe and record an overall image including the peripheral portion of the eye to be examined simultaneously with the lesion portion of the eye on the basis of the illumination light from the second illumination system.

According to a second aspect of the invention, there is provided a slit lamp microscope characterized by comprising: a first illumination system for projecting local illumination light to an eye to be examined for observing a partial image of the eye to be examined; a second illumination system for illuminating the overall eye to be examined for enabling to observe the overall image of the ovservatin portion; an imaging means for imaging a partial image of the eye observed and projected by said first illumination system and the overall image projected by said second illumination system to obtain the partial image and the overall image of the eye to be examined; and an image processing means for synthesizing and displaying the partial image and the overall image obtained by said imaging means.

According to this aspect, the partial image of the eye to be examined is observed by projecting the local illumination light to the eye to be examined by the first illumination system, at the same time, the overall image of the eye to be examined is illuminated by the second illumination system, the partial image of the eye to be observed and illuminated by the first illumination system and the overall image illuminated by the second illumination system are picked up by the imaging means, and the partial image and the overall image obtained by the imaging means are synthesized and displayed by the image processing means.

Accordingly, it is possible to observe the synthetic image clearly for the overall image and the partial image such as a lesion portion of the eye to be examined.

According to a third aspect of the invention, in the slit lamp microscope in accordance with the first or second aspect, the illumination field limiting mechanism portion of the second illumination system is characterized by including a plurality of illumination field limiting members having different limit ranges of the illumination field of the illumination light projected to the peripheral portion of the eye to be examined, the illumination field limiting members being selectively disposed in an optical path of the second illumination system.

According to this aspect, since, by means of the illumination field limiting mechanism portion of the second illumination system, the plurality of illumination field limiting members having different limit ranges of the illumination field of the illumination light projected to the peripheral portion of the eye to be examined are selectively disposed in the optical path of the second illumination system, it is possible to change the illumination fields of the illumination light projected to the peripheral portion of the eye to be examined by suitably selecting the plurality of illumination field limiting members, and it is possible to clearly illuminate the peripheral portion corresponding to various sizes of the medically damaged portions of the eyes to be observed by the first illumination system.

DESCRIPTION OF THE PREFERRED EMBODIMENTS

An embodiment of the present invention will now be described with reference to the accompanying drawings.

Figure 1:
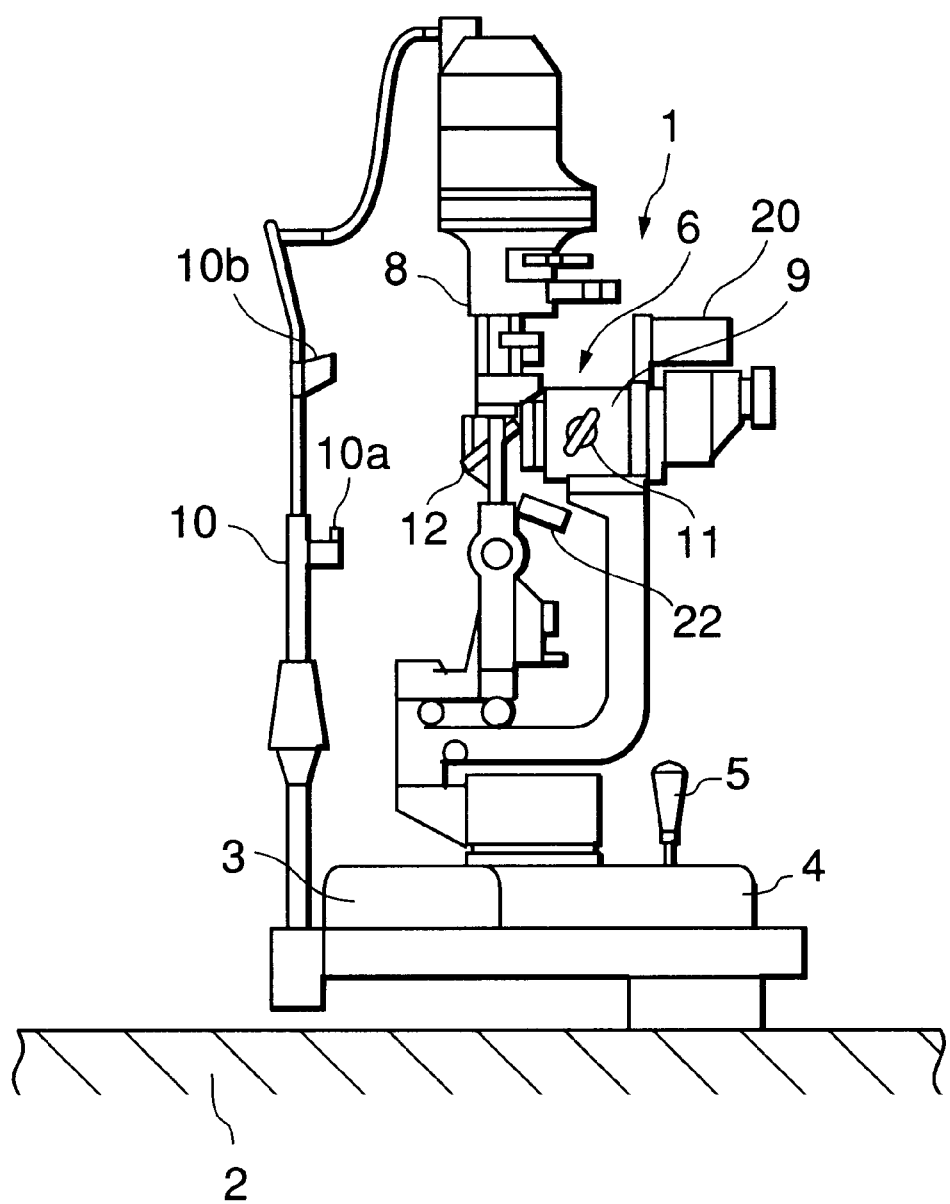
FIG. 1 is a side elevational view showing an overall slit lamp microscope according to a first embodiment of the present invention.

A slit lamp microscope in accordance with an embodiment shown in FIG. 1 is provided with a base 4 which is supported movably in a horizontal lateral direction and in a horizontal perpendicular direction through a moving mechanism section 3 on a table 2, an operation handle 5 for moving the base 4 in the horizontal lateral direction and in the horizontal perpendicular direction by a slant tilting operation, an observation optical system 6 supported to the above-described base 4, respectively, an illumination system 8 disposed to face a light source and a lens sleeve body with a slit, and a jaw receiving base 10 having a jaw receiving portion 10a for a patient to face with the lens sleeve body 9 receiving an objective lens of a microscope system 6 and a foreface abutment 10b.

A rotary shaft is projected from a side wall of the above-described lens sleeve body 9 for changing or zooming an observation magnification. An operating knob 11 provided with figures such as 6, 10, 16, 25, 40 and the like indicating the observation magnification of the microscope system 9 is mounted on an outer periphery of the rotary shaft.

Figure 2:
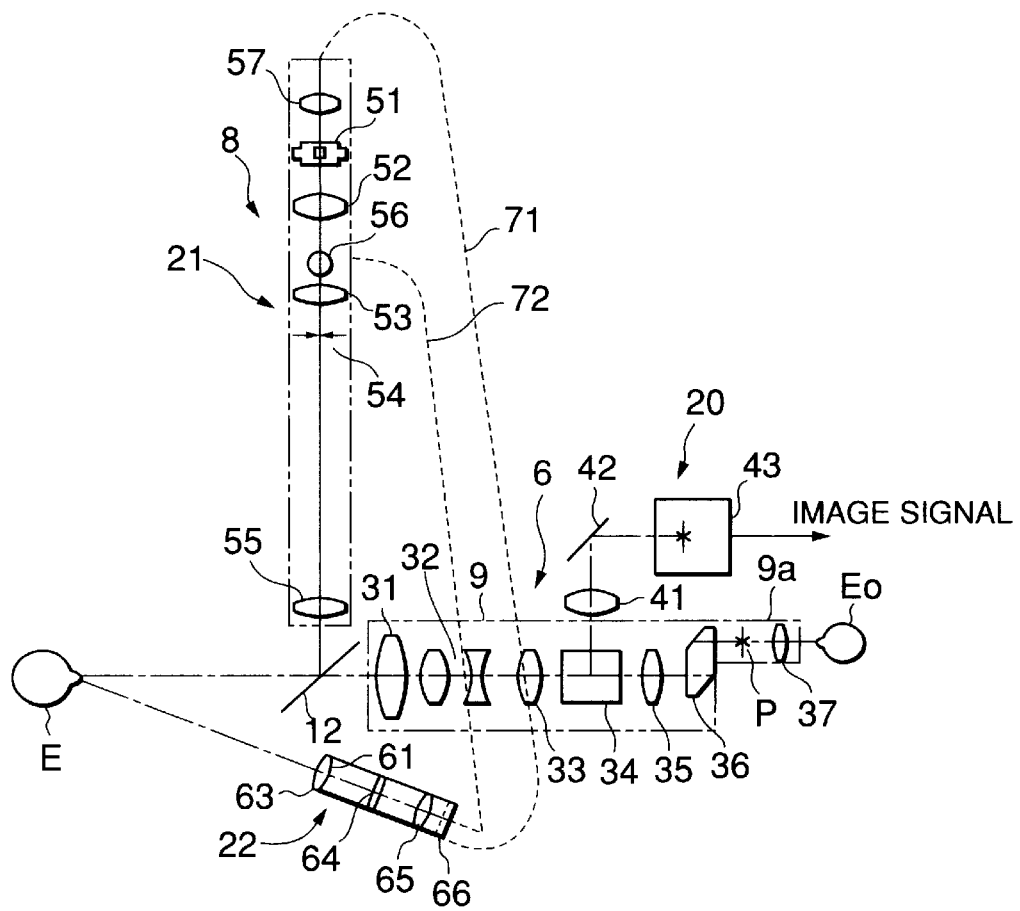
FIG. 2 is a schematic view showing a structure of the slit lamp microscope according to the first embodiment of the invention.

FIG. 2 is a schematic view showing an optical system of a slit lamp microscope 1 in accordance with the embodiment of the present invention. This slit lamp microscope 1 has the observation optical system 6 received in the lens sleeve body 9, a pickup device 20 mounted on the lens sleeve body 9, a first illumination system 21 constituting the above-described illumination system 8 and disposed perpendicular to a half-mirror 12 facing the eye E to be examined, and a second illumination system 22 constituting the microscope system 6 and disposed in the vicinity of the above-described half-mirror 12.

The observation optical system 6 is provided with the half-mirror 12, the objective lens 31, a zooming optical system 32, a condenser lens 33, a beam splitter 34, a relay lens 35, a prism 36 for changing the optical path on the side of the ocular ophthalmic lens sleeve 9a and an ocular lens 37 disposed in the ocular ophthalmic lens sleeve 9a. The image of the eye E to be examined is formed on an imaging point p shown in FIG. 2 and may be observed by the eye Eo of the examiner.

The above-described pickup 20 is provided with a condenser lens 41 for converging a light flux branched from the above-described beam splitter 34, a mirror 42 for bending the light flux from the condenser lens 41 in a direction perpendicular at a right angle, and a pickup camera 43.

The first illumination system 21 constituting the above-described illumination system 8 is provided with the light source 51 such as a halogen lamp or the like, condenser lenses 52 and 53 for converging the light from the light source 51, a slit 54 for allowing only a part of the light passing through the condenser lenses 52 and 53 to pass through the slit 54 itself, a condenser lens 55 for converging the light that has passed through the slit 54, a strobe light source 56 such as a xenon lamp or the like disposed between the light source 51 and the condenser lens 52, and an auxiliary condensor lens 57 disposed on the opposite side to the condensor lens 52 after the above-described light source 51.

Figure 5:
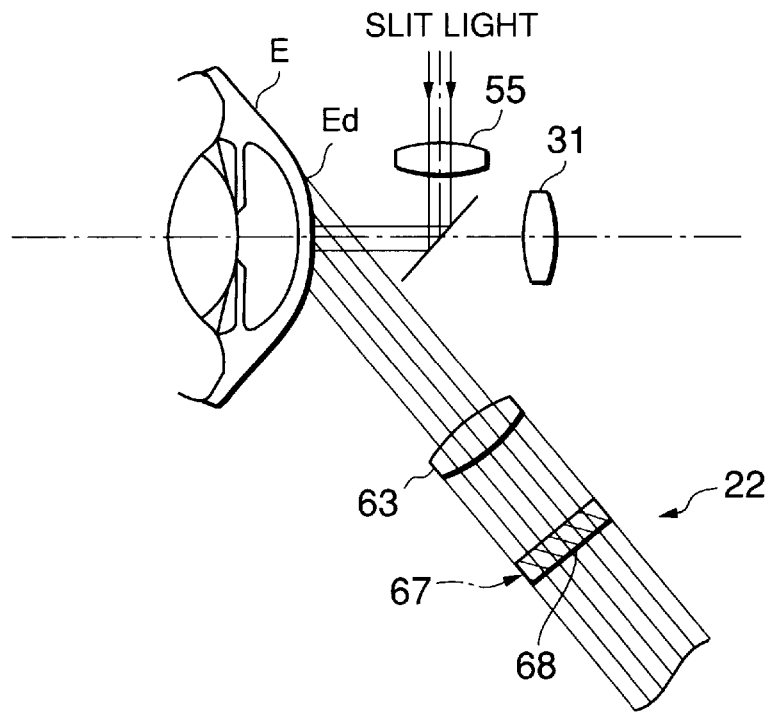
FIG. 5 is an illustration of the illumination light by the first illumination system and the illumination condition of the slit light by the first illumination system in the slit lamp microscope according to the first embodiment of the invention.
Figure 6:
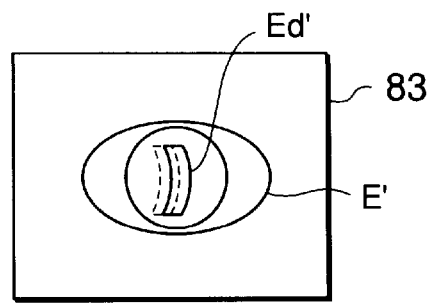
FIG. 6 is an illustration of the image of the eye to be examined corresponding to FIG. 5.

The above-described slit 53 and the eye E to be examined are located in a conjugative position relative to the condensor lens 55 so that a local illumination ray of light (hereinafter referred to as "slit light") is projected to, for example, the cornea of the eye E to be examined through the above-described half-mirror 12 as shown in FIG. 5. The image of the corneal cross section Ed (indicated by hatching in FIG. 5) which is a part of the partial image of the eye E to be examined is observed as shown in FIG. 6.

The second illumination system 22 constituting the above-described illumination system 8 is provided with an auxiliary lens sleeve 61 to face the eye E to be examined in the vicinity of the above-described half-mirror 12. An illumination lens 63, a diaphragm 64 used as an illumination field limiting mechanism, a condenser lens 65 and a shutter 66 are disposed in order from an end face, facing the eye E to be examined of the auxiliary lens sleeve 61. At the same time, the respective light emission ends of a first light guide 71 using an optical fiber derived from the vicinity of the auxiliary condensor lens 57 of the first illumination system 21 and a second light guide 72 using an optical fiber derived from the vicinity of the above-described strobe light source 55 are disposed to face the end face on the side of the condensor lens 65 of the auxiliary lens sleeve 61.

Figure 3:
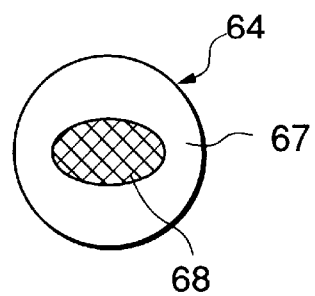
FIG. 3 is an enlarged view showing an example of an illumination field limiting mechanism portion in the slit lamp microscope according to the first embodiment of the invention.

FIG. 3 shows an example of the above-described diaphragm 64. A light shielding portion 68 for interrupting the light is provided by a deposition or the like to a central part of, for example, a light-transmissive, disc-shaped, transparent glass plate 67 perpendicular to the optical path within the above-described auxiliary lens sleeve 61.

Figure 4:
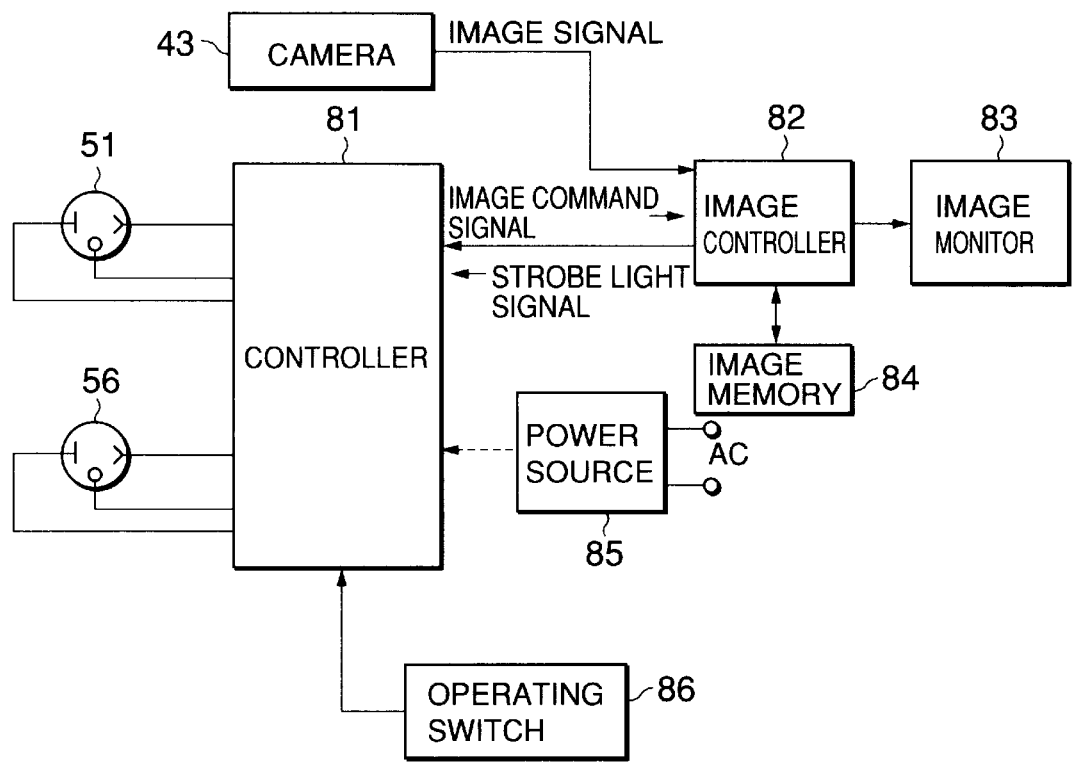
FIG. 4 is a block diagram showing a primary part of a control system of the slit lamp microscope according to the first embodiment of the invention.

FIG. 4 shows a primary part of a control system for the slit lamp microscope 1, which is provided with a control section 81 for controlling the above-described light source 51 and the strobe light source 55 or the like, an image control section 82 for receiving an image signal from the above-described pickup camera 43, an image monitor 83 such as a liquid crystal display connected to this image control section 82, an image memory 84 which is a memory means connected to the image control section 82, a power source 85 for feeding an electric power to be needed for the operation of the above-described slit lamp microscope 1 as a whole, and an operating switch 86 for feeding an operation signal to the above-described control section 81.

Then, the operation signal is fed to the light emission control section 81 by the operating switch 82, and the pickup command signal is fed from the control section 81 to the image control section 82. At the same time, the strobe emission signal is fed from the image control section 82 to the above-described control section 81. As a result, the above-described strobe light source is irradiated on the basis of the control of the control section 81.

The operation of the above-described slit lamp microscope 1 will now be described with reference to the drawings also including FIGS. 5 and 6.

The light irradiated from the light source 51 within the first illumination system 21 projects the slit 54 through the condenser lens 52. Since the slit 54 and the eye E to be examined are disposed in the conjugative position, the slit light passed and formed through the slit 54 is projected to the corneal cross section (indicated by the hatching) Ed of the eye E to be examined as shown in, for example, FIG. 5 through the condenser lens 55 and the half-mirror 12.

On the other hand, the light that has been irradiated from the above-described light source 51 and converged by the auxiliary condenser lens 57 is introduced to the condenser lens 65 of the second illumination system 22 through the above-described first light guide 71 and is projected to the peripheral portion around the corneal cross section Ed of the eye E to be examined through the illumination lens 63 under the condition that the central portion of the light flux is interrupted by the above-described shielding portion 68 through the diaphragm 64.

Namely, since the above-described diaphragm 64 is disposed in the conjugative position with the eye E to be examined, almost all the eye E to be examined is projected with a brightness distribution in response to the condition of the light shielding portion 68.

Accordingly, the entire portion of the eye E to be examined (mainly the peripheral portion (iris portion or the like)) is illuminated by the second illumination system 22.

Thus, the light projected to the eye E to be examined and reflected at the corneal cross section Ed of the eye E to be examined and the light flux reflected at the overall eye E to be examined are introduced into the above-described half-mirror 12 and objective lens 31 of the observation optical system 6. Furthermore, a part thereof is imaged at the imaging point p shown in FIG. 2 through the beam splitter 34 and observed by the eye Eo of the examiner.

Also, the light flux branched from the beam splitter 34 is introduced into the pickup camera 43 through the above-described mirror 42 so that the same observation image as that for the eye Eo of the examiner is picked up by the pickup camera 43 and fed to and displayed on the image monitor 83 on the bais of the control of the above-described control section 82.

This image, i.e., the corneal cross sectional image Ed' by the slit light may be observed under the condition that a good contrast may be maintained as shown in FIG. 6. At the same time, also the overall image E' including the iris or the like in the eye E to be examined may be clearly observed. It is therefore possible to observe the lesion portion while catching up with the overall image of the eye E to be examined.

Also, it is of course possible to close the shutter 66 of the second illumination system 22, interrupt the light to the eye E to be examined from the second illumination system 22 and observe and pick up the eye E to be examined only with the slit light from the first illumination system 21.

Incidentally, when the eye E to be examined is to be picked up in the form of the image, on the control basis of the above-described control section 81, the above-described strobe light source 56 is irradiated in addition to the irradiation of the light source 51. The light is introduced through the second light guide 72 to the second illumination system 22, and the peripheral portion of the corneal cross section Ed of the eye E to be examined is mainly illuminated by the second illumination system 22. Accordingly, also, the peripheral portion of the corneal cross section Ed of the eye E to be examined is picked up and recorded by the pickup camera 43 into a good conditioned image that is the same as that observed by the eye Eo of the examiner.

A second embodiment of the present invention will now be described with reference to FIGS. 7 and 8.

Figure 7:
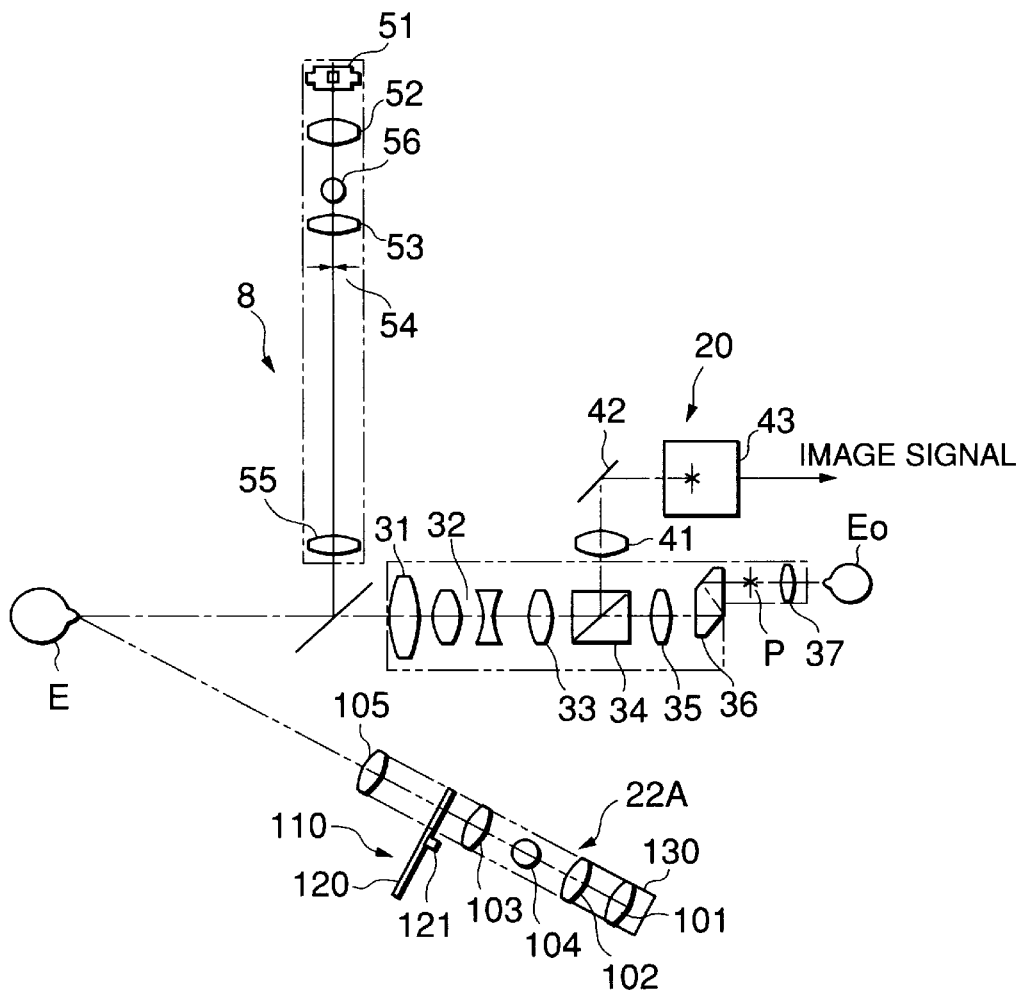
FIG. 7 is a schematic view showing a structure of a slit lamp microscope according to a second embodiment of the invention.

In the slit lamp microscope 1A in accordance with the second embodiment shown in FIG. 7, since the basic construction of the optical system is the same as the case of the slit lamp microscope 1 in accordance with the first embodiment, the same reference numerals are used to indicate the like components as those in the slit lamp microscope 1 in accordance with the first embodiment, and it detailed explanation will be omitted in order to avoid any duplication.

The slit lamp microscope 1A according to the second embodiment is characterized in that the auxiliary condensor lens 57 of the first illumination system is dispensed with as the first illumination system 21A, the second illumination system 22A is provided with a light source 101 such as a halogen lamp or the like, condensor lenses 102 and 103 for converging the light from the light source 101, a strobe light source 104 such as a xenon lamp or the like disposed between the above-described condenser lenses 102 and 103, a diaphragm 110 as a illumination field limiting mechanism and a projection lens 105, and the above-described first and second light guides 71 and 72 are dispensed with.

Also, the control system is the same as that of the first embodiment. The light source 101 and the strobe light source 104 are turned on and controlled by the controller 81 which is the same as in the first embodiment.

Figure 8:
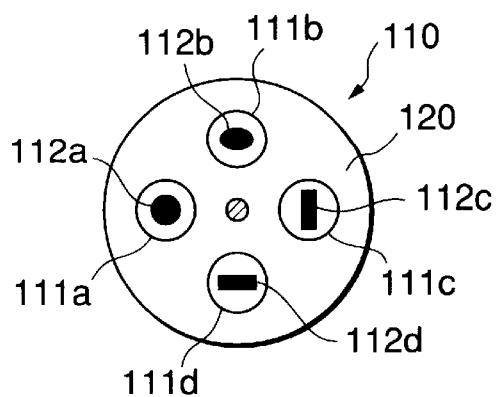
FIG. 8 is an enlarged view showing an illumination field limiting mechanism portion in the slit lamp microscope according to the second embodiment of the invention.
Figure 9:
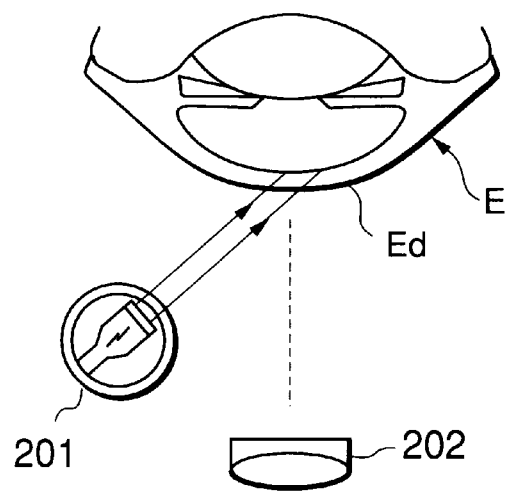
FIG. 9 is an illustration showing an illumination condition of slit light in a conventional slit lamp microscope.
Figure 10:
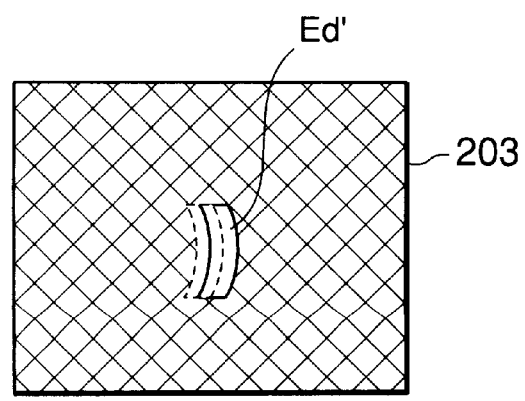
FIG. 10 is an illustration of an observed image in the conventional slit lamp microscope.

For example, as shown in FIG. 8, the diaphragm 110 as the illumination field limiting mechanism is composed of four light-transmissive, disc-shaped transparent glass plates 111a to 111d disposed in a circular position on a rotary base plate 120. Light shielding portions 112a to 112d which are the illumination limiting members are provided in a central portion of each transparent glass plate 111a to 111d.

Then, the rotary base plate 120 is disposed perpendicular to the optical path within the auxiliary lens sleeve 130 and a central portion of the rotary base plate 120 is rotatable in the vicinity of the auxiliary lens sleeve 130 by a support member 121 so that any one of the transparent glass plates 111a to 111d of the rotary base plate 120 may be selectively disposed in the optical path within the auxiliary sleeve 130.

As shown in FIG. 8, the above-described light shielding portions 112a to 112d are formed into, for example, a circular shape, an elliptical shape, a longitudinal rectangular shape and a laterally elongated rectangular shape, respectively for limiting the illumination field relative to the eye E to be expected by the second illumination system 22B in response to each shape.

The above-described rotary base plate 120 may be formed so that any one of the transparent glass plates 111a to 111d may be manually rotated to be selectively disposed in the optical path within the auxiliary lens sleeve 130 or the rotary base plate 120 may be rotated at a predetermined time interval by using a motor and a speed reduction mechanism or the like so that any one of the transparent glass plates 111a to 111d may be selectively disposed in the optical path within the auxiliary lens sleeve 130.

The operation of the above-described slit lamp microscope 1A will be described with reference to the drawings including FIG. 4 illustrating the controlling system.

Under the condition that any one of the transparent glass plates 111a to 111d is disposed in the optical path within the auxiliary lens sleeve 130, the light source 51 within the first illumination system 21 is irradiated. The light from the light source 51 projects the slit 54 through the condenser lens 52. Since the slit 54 and the eye E to be examined are disposed in the conjugative position, the slit light passed through and formed by the slit 54 projects the corneal cross section Ed of the eye E to be examined through the condensor lens 55 and the half-mirror 12 as shown in, for example, FIG. 5.

Subsequently, when the examiner pushes the operating switch 86, the control section 81 feeds the imaging command signal to the image control section 82.

The image control section 82 feeds the storbe emission signal to the control section 81 in synchronism with the image signal from the imaging camera 43. Thus, the control section 81 irradiates the above-described strobe light source 56. At the same time, the imaging camera 43 operates, and the image of the corneal cross section Ed of the eye E to be examined is picked up. The picked up corneal cross section image Ed' is stored in the image memory 84.

Subsequently, the light source 101 irradiates on the basis of the control of the above-described control section 81. The light from the light source 101 is projected onto the peripheral portion of the corneal cross section Ed of the eye E to be examined through the projection lens 105 under the condition that a central portion of the light flux is shielded by, for example, the above-described light shielding portion 112a (under the condition that the illumination field is limited) passing through the diaphragm 110.

In a predetermined period of time from the picking-up of the corneal cross section image Ed' by the imaging camera 43 (in a lapse of time corresponding to one frame), the control section 81 again feeds the imaging command signal to the image control section 82. The image control section 82 irradiates the storbe light source 104 of the second illumination system 22B in response to the second imaging command signal in synchronism with the image signal from the imaging camera 43. At the same time, the imaging camera 43 again operates so that the peripheral portion image Ed' of the corneal cross section Ed of the eye E to be examined is picked up. The picked up peripheral portion of the image Ed of corneal cross section Ed is stored in the image memory 84.

As a result, only by one operation of the operating switch 86, the corneal cross section image Ed' of the eye E to be examined on the basis of the operation of the first illumination system 21A and the peripheral portion image E' of the corneal cross section Ed of the eye E to be examined on the basis of the operation of the second illumination system 22B are recorded in order in a very short period of time in the image memory 84.

Thus, the two images are recorded with a very short time difference so that the regions of the two images corresponds to each other substantially in one-to-one relation.

The above-described image control section 82 synthesizes and superimposes the two images recorded in the image memory 84 and represents them as a single image on the image field of the image monitor 83 in the same manner as in the case shown in FIG. 6.

Thus, also in the second embodiment, the corneal cross section image Ed' may be observed under the condition that the contrast is kept well, and at the same time, also the overall image including the peripheral portion such as an iris or the like in the eye E to be examined may be clearly observed. It is therefore possible to observe the lesion portion while knowing the overall image of the eye E.

In accordance with a first aspect of the invention, a slit lamp microscope is provided in which it is possible to observe and record the clear image of the lesion portion of the eye to be examined with a high contrast on the basis of the local illumination light, and it is possible to observe and record the overall image including the peripheral portion of the eye to be examined simultaneously with the lesion portion of the eye on the basis of the illumination light from the second illumination system.

In accordance with a second aspect of the invention, a slit lamp microscope is provided in which it is possible to observe a clear synthetic image of the lesion portion of the eye to be examined and the overall image.

In accordance with a third aspect of the invention, it is possible to provide a slit lamp microscope that may illuminate the peripheral portion corresponding to various sizes of the lesion portions of the eyes to be examined.

What is claimed is:

1. A slit lamp microscope comprising:
   a first illumination system further comprising:
      a first illumination means for lighting an object;
      a first condenser lens for converging light downstream from the first illumination means; and
      a slit for the passage of light from the first illumination means to the object, the slit being downstream from the condenser lens;
   wherein the first illumination system is for projecting local illumination light onto an object such as an eye to be examined for observing a focus point of the slit lamp microscope which is a cross section of an observation portion of the eye to be examined; and a second illumination system further comprising:
  a second illumination means for lighting the object;
  a second condenser lens for converging light downstream from the second illumination means; and
  an illumination field limiting mechanism for blocking light from the second illumination means directed toward the focus point of the slit lamp microscope;
wherein a portion peripheral to the cross section of the observation portion of the illumination field of the eye to be examined by said first illumination system is illuminated for enabling the simultaneous observation of the peripheral portion of the observation portion.

2. The slit lamp microscope according to claim 1, wherein said illumination field limiting mechanism portion of said second illumination system includes a plurality of illumination field limiting members having different limit ranges of the illumination field of the illumination light projected to the peripheral portion of the eye to be examined, said illumination field limiting members being selectively disposed in an optical path of said second illumination system.

3. A slit lamp microscope comprising:
  a first illumination system further comprising:
    a first illumination means for lighting an object;
    a first condenser lens for converging light downstream from the first illumination means; and
    a slit for the passage of light from the first illumination means to the object, the slit being downstream from the condenser lens;
  wherein the first illumination system is for projecting local illumination light to an eye to be examined for observing a focus point of the slit lamp microscope;
  a second illumination system further comprising:
    a second illumination means for lighting the object;
    a second condenser lens for converging light downstream from the second illumination means; and
    an illumination field limiting mechanism for blocking light from the second illumination means directed toward the focus point of the slit lamp microscope;
  wherein the second illumination system is for illuminating the periphery of the focal point of the slit lamp microscope,
  an imaging means for imaging, one after another with a time lag, the focus point of the slit lamp microscope projected by said first illumination system and the periphery of the focal point of the slit lamp microscope projected by said second illumination system to obtain a partial image and an overall image of the eye to be examined; and
  an image processing means for synthesizing and displaying the partial image and the overall image each obtained at different times by said imaging means.

* * * * *